US010278833B2

(12) United States Patent
Howard et al.

(10) Patent No.: US 10,278,833 B2
(45) Date of Patent: May 7, 2019

(54) CENTER LORDOTIC MESH CAGE

(71) Applicant: GLOBUS MEDICAL, INC., Audubon, PA (US)

(72) Inventors: George Howard, Green Lane, PA (US); Jason Gray, East Greenville, PA (US)

(73) Assignee: Globus Medical, Inc., Audubon, PA (US)

( * ) Notice: Subject to any disclaimer, the term of this patent is extended or adjusted under 35 U.S.C. 154(b) by 267 days.

(21) Appl. No.: 15/264,974

(22) Filed: Sep. 14, 2016

(65) Prior Publication Data
US 2018/0071107 A1    Mar. 15, 2018

(51) Int. Cl.
*A61F 2/44* (2006.01)
*A61F 2/30* (2006.01)

(52) U.S. Cl.
CPC .............. *A61F 2/446* (2013.01); *A61F 2/44* (2013.01); *A61F 2/4465* (2013.01); *A61F 2002/30235* (2013.01); *A61F 2002/30504* (2013.01); *A61F 2002/30599* (2013.01); *A61F 2002/30604* (2013.01); *A61F 2002/448* (2013.01); *A61F 2002/4415* (2013.01); *A61F 2002/4475* (2013.01); *A61F 2220/0016* (2013.01)

(58) Field of Classification Search
CPC .......... A61F 2/44; A61F 2/4455; A61F 2/446; A61F 2/4465; A61F 2002/4475; A61F 2002/448; A61F 2002/4485; A61F 2002/4495
See application file for complete search history.

(56) References Cited

U.S. PATENT DOCUMENTS

| | | | | |
|---|---|---|---|---|
| 5,192,327 A | * | 3/1993 | Brantigan | A61F 2/44 606/247 |
| 5,534,029 A | * | 7/1996 | Shima | A61F 2/44 606/247 |
| 5,571,190 A | * | 11/1996 | Ulrich | A61F 2/44 606/247 |
| 5,609,637 A | * | 3/1997 | Biedermann | A61F 2/442 623/17.16 |
| 5,702,451 A | * | 12/1997 | Biedermann | A61F 2/30744 606/247 |
| 5,897,556 A | * | 4/1999 | Drewry | A61B 17/8085 606/247 |
| 5,989,290 A | * | 11/1999 | Biedermann | A61F 2/44 606/246 |
| 6,086,613 A | * | 7/2000 | Camino | A61F 2/44 623/17.16 |
| 6,159,211 A | | 12/2000 | Boriani et al. | |
| 6,200,348 B1 | * | 3/2001 | Biedermann | A61F 2/44 606/247 |
| 6,719,796 B2 | * | 4/2004 | Cohen | A61F 2/44 623/17.15 |

(Continued)

*Primary Examiner* — Eric S Gibson

(57) ABSTRACT

An implant assembly including an angled intermediate plate inserted between two sections of mesh cage. The intermediate plate offers a safe and secure connection to the mesh cages while providing lordosis/kyphosis angling at the center of the construct instead of at the end of the cage only. One or more angled endplates may be included which allow the surgeon to make a construct unique to the patient's anatomy. The endplates and intermediate plate may include integrated clips configured to snap into corresponding holes in the mesh cage for a secure fit.

15 Claims, 4 Drawing Sheets

(56) References Cited

U.S. PATENT DOCUMENTS

| | | | | |
|---|---|---|---|---|
| 6,758,862 B2* | 7/2004 | Berry | | A61F 2/44 606/247 |
| 6,776,798 B2 | 8/2004 | Camino et al. | | |
| 6,899,734 B2* | 5/2005 | Castro | | A61F 2/4465 623/17.16 |
| 6,991,653 B2* | 1/2006 | White | | A61F 2/44 606/247 |
| 7,309,358 B2* | 12/2007 | Berry | | A61F 2/44 606/86 A |
| 7,473,277 B2* | 1/2009 | Boyer, II | | B29C 43/006 623/17.11 |
| 7,591,852 B2* | 9/2009 | Prosser | | A61F 2/4465 623/17.11 |
| 7,887,594 B2* | 2/2011 | Berry | | A61F 2/4455 606/249 |
| 8,920,502 B1* | 12/2014 | Muhanna | | A61F 2/44 623/17.16 |
| 9,023,107 B2* | 5/2015 | Muhanna | | A61F 2/442 623/17.15 |
| 9,700,425 B1* | 7/2017 | Smith | | A61B 17/025 |
| 2003/0191531 A1* | 10/2003 | Berry | | A61F 2/44 623/17.11 |
| 2004/0073314 A1* | 4/2004 | White | | A61F 2/44 623/17.15 |
| 2005/0060034 A1* | 3/2005 | Berry | | A61F 2/44 623/17.11 |
| 2006/0241762 A1* | 10/2006 | Kraus | | A61F 2/44 623/17.11 |
| 2007/0129805 A1* | 6/2007 | Braddock, Jr. | | A61F 2/30744 623/17.11 |
| 2007/0255410 A1* | 11/2007 | Dickson | | A61F 2/44 623/17.11 |
| 2007/0270957 A1* | 11/2007 | Heinz | | A61F 2/44 623/17.11 |
| 2009/0036985 A1* | 2/2009 | Whiting | | A61F 2/30744 623/17.11 |
| 2009/0112325 A1* | 4/2009 | Refai | | A61F 2/30734 623/17.16 |
| 2009/0138089 A1* | 5/2009 | Doubler | | A61F 2/44 623/17.16 |
| 2011/0106258 A1 | 5/2011 | Blackwell et al. | | |
| 2011/0251691 A1 | 10/2011 | McLaughlin et al. | | |
| 2014/0207235 A1 | 7/2014 | Drapeau | | |
| 2018/0071107 A1* | 3/2018 | Howard | | A61F 2/446 |
| 2018/0098861 A1* | 4/2018 | Howard | | A61F 2/44 |

* cited by examiner

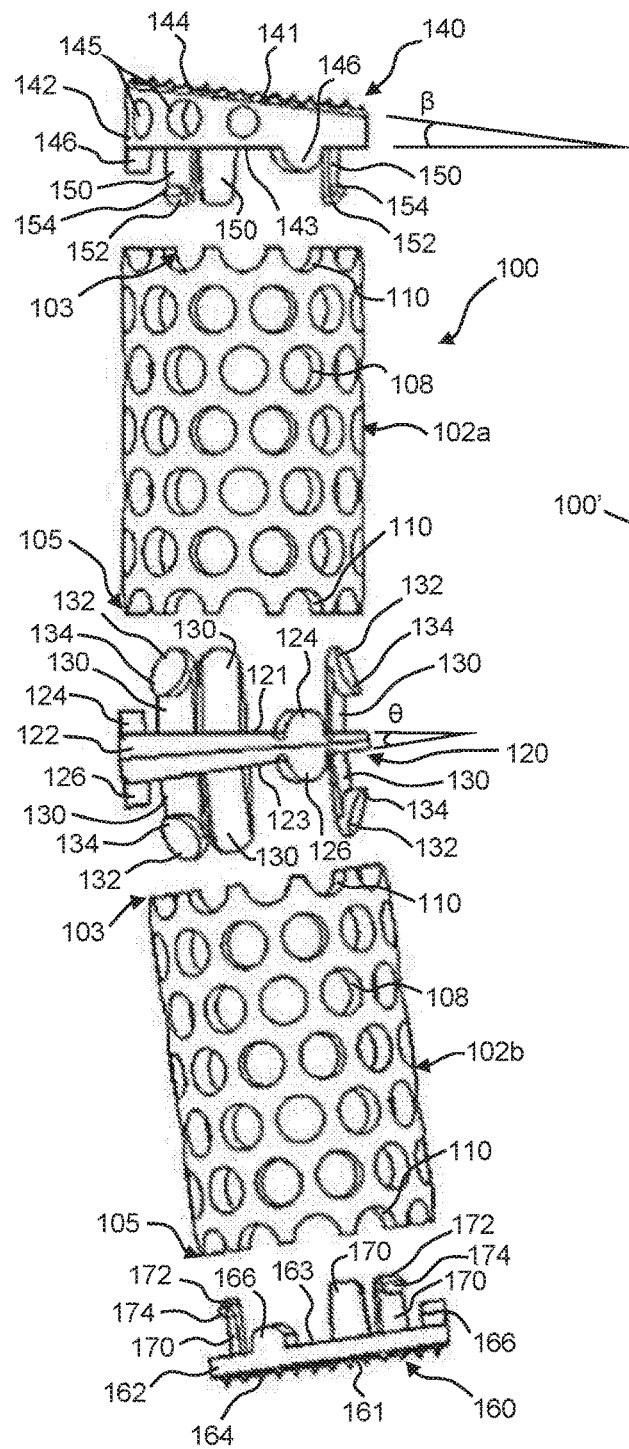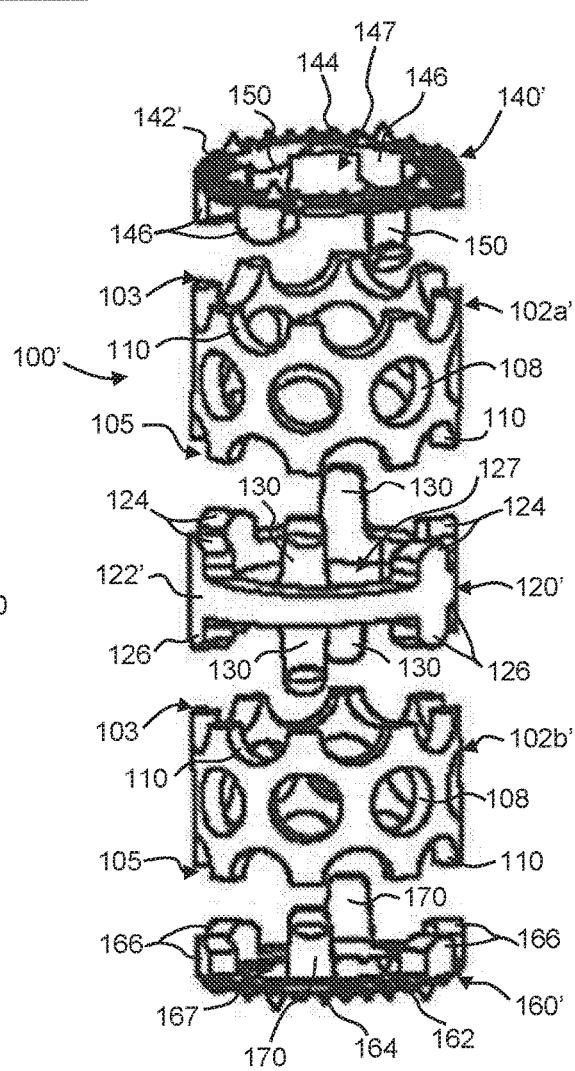
Fig. 6
Fig. 7

CENTER LORDOTIC MESH CAGE

FIELD

The present disclosure relates to systems and devices for supporting the spine after removal of at least a part of a vertebra. More particularly, the disclosure relates to vertebral body replacement implant assemblies and attachment assemblies.

BACKGROUND

Diseases and injury to bone structures, such as the vertebral column, and conditions requiring surgical intervention are relatively common. A variety of conventional implant or graft devices are presently available for use in specific areas. The devices vary in size, shape, materials used, and insertion techniques. For example, in the vertebral column, grafts may provide restoration, decompression, or stabilization of the spine. Typically these devices include a member that is inserted in the vertebral column to replace an injured portion. An example of such a procedure is a corpectomy, which involves the replacement of a vertebral body with an implant or graft. One exemplary graft is a mesh corpectomy cage which is secured to the adjacent vertebrae via end plates to maintain the position of the implant in situ.

While these conventional devices may generally provide adequate results, they have several disadvantages. For example, often with a corpectomy that involves more than one level, the center segment of the corpectomy cage will settle into a position very close to the patient's dura and spinal cord due to the natural lordosis/kyphosis of the patient. Such proximity to the dura and spinal cord may cause pain, discomfort or further damage to the vertebral column.

Additionally, the endplates are typically secured to the cage with screws. The screws are often cumbersome to install and also make it more difficult to safely remove and replace any component of the construct. Furthermore, there is an inherent risk that the screws may be dropped during a procedure.

SUMMARY

To meet these and other needs, devices and systems for providing vertebral body replacement are provided. In particular, an implant assembly in accordance with an embodiment of the disclosure includes an angled intermediate plate which that can be inserted between two sections of mesh cage. The intermediate plate offers a safe and secure connection to the mesh cages while providing lordosis/kyphosis at the center of the construct instead of at the end of the cage only. This allows for the body of the cage to be moved away from the dura and spinal cord of the patient.

In at least one embodiment, an implant assembly in accordance with the disclosure includes one or more angled endplates which allow the surgeon to make a construct unique to the patient's anatomy. The endplates and intermediate plate may be accurately centered to each other and the mesh cages by means of the radial holes in the mesh cage. Integrated clips machined on the endplates and intermediate plate may be configured to snap into corresponding holes in the mesh cage for a secure fit. The quick clip system makes a secure construct while allowing for components to be removed and replaced prior to insertion into the body should the need arise.

BRIEF DESCRIPTION OF THE DRAWINGS

The accompanying drawings, which are incorporated herein and constitute part of this specification, illustrate the presently preferred embodiments of the disclosure, and, together with the general description given above and the detailed description given below, serve to explain the features of the disclosure. In the drawings:

FIG. 6 is an exploded perspective view of the implant assembly of FIG. 1.

FIG. 7 is an exploded perspective view of another exemplary implant assembly.

DETAILED DESCRIPTION

Figure 1:
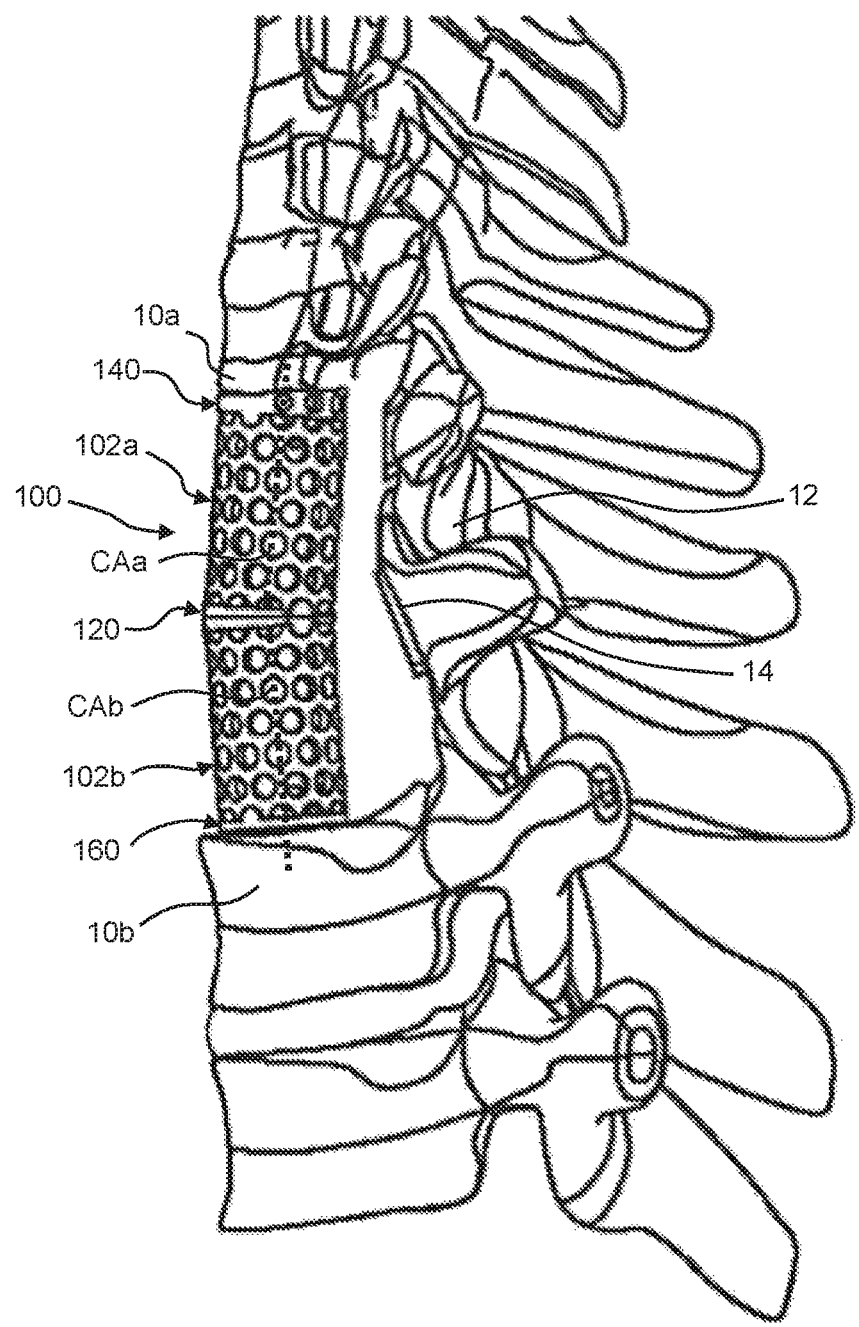
FIG. 1 is a side elevation view of an implant assembly according to an exemplary embodiment attached between vertebrae.

In the drawings, like numerals indicate like elements throughout, with alphabetical or prime identifiers indicating a particular one of the more generally identified element. Certain terminology is used herein for convenience only and is not to be taken as a limitation on the present invention. The following describes preferred embodiments of the present disclosure. However, it should be understood, based on this disclosure, that the invention is not limited by the preferred embodiments described herein.

Referring to FIG. 1, an exemplary implant assembly 100 in accordance with an embodiment of the disclosure is illustrated positioned between a pair of vertebrae 10a, 10b. The implant assembly 100 generally includes two or more mesh cages 102a, 102b, at least one intermediate plate 120 and a pair of endplates 140, 160. The intermediate plate 120 is secured between the cages 102a, 102b and has an angled configuration such that the central axis CAa of the cage 102a is angled at an acute angle $\alpha$ (see FIG. 9) relative to the central axis Cab of the cage 102b. The endplate 140 is secured to the end of cage 102a and secures the cage 102a to the adjacent vertebrae 10a. The endplate 160 is secured to the end of cage 102b and secures the cage 102b to the adjacent vertebrae 10b. The lordotic angle $\alpha$ created by the intermediate plate 120 helps to align the ends of the cages 102a, 102b with the vertebral endplates 10a, 10b which will help in minimizing subsidence. The lordotic angle $\alpha$ also positions the cages 102a, 102b away from the dura 14 and spinal cord 12 of the patient.

Figure 2:
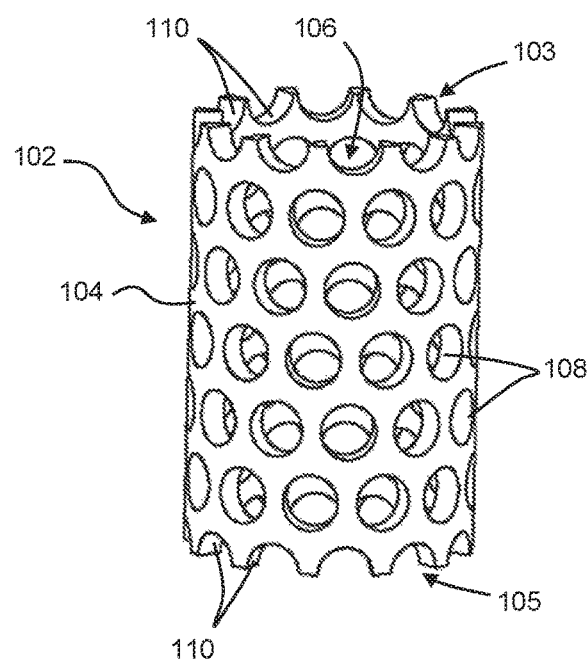
FIG. 2 is a perspective view of exemplary cage member of the implant assembly of FIG. 1.
Figure 3:
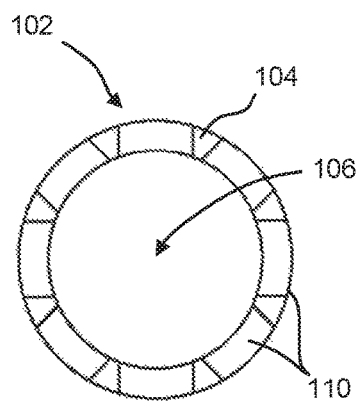
FIG. 3 is a top plan view of the cage member of FIG. 2.
Figure 4:
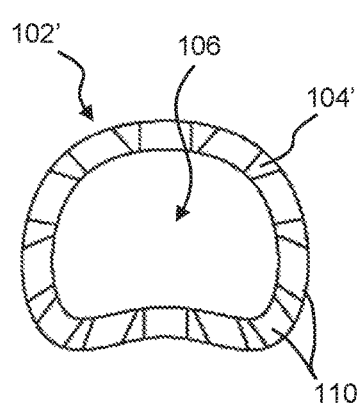
FIG. 4 is a top plan view of an alternative cage member.
Figure 5:
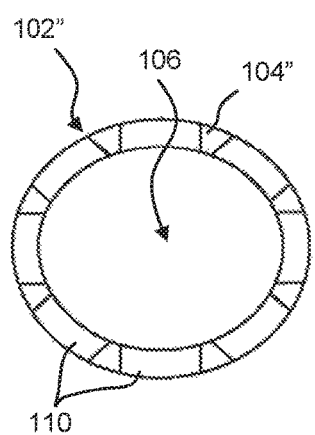
FIG. 5 is a top plan view of yet another alternative cage member.

Referring to FIGS. 2-5, exemplary embodiments of the cage 102 will be described. Each cage 102 generally has a hollow tubular body 104 extending between ends 103, 105 with a passage 106 therethrough. The tubular body 104 may be manufactured from various materials, for example, but not limited to, titanium or other metals, carbon fibers, ceramics, polymers or biocomposites. As illustrated in the embodiment of FIGS. 2 and 3, the exemplary cage 102 has a circular cross-section, however, the cage 102 may have various configurations. As two non-limiting examples, the cage 102' illustrated in FIG. 3 has a kidney shaped cross-section and the cage 102″ illustrated in FIG. 4 has an oval cross-section. The mesh cages 102 may be supplied at various convenient lengths or can be cut to size. It is understood that the cages 102*a*, 102*b* of the implant assembly 100 may have the same or different lengths.

The tubular body 104 defines a series of radial openings 108 which open into the through passage 106. The radial openings 108 facilitate bone ingrowth and provide connection points for clips on the intermediate plate 120 and the endplates 140, 160, as will be described in more detail hereinafter. The openings 108 are preferably evenly spaced about the tubular body 104 to create a mesh thickness that offers compressive and torsional strength while allowing the cage to be easily cut to length. While the openings 108 are illustrated with a circular configuration, they openings 108 may have other shapes, for example, square or octagon.

Each end 103, 105 of the cage 102 includes a series of end openings 110 which open into the through passage 106 and are also open to the respective end surface of the tubular body 104. The end openings 110 are configured to receive tabs extending from the intermediate plate 120 and the endplates 140, 160 to provide rotational stability. While the end openings 110 are illustrated with a semi-circular configuration, they openings 108 may have other shapes, for example, square or octagon, and may have a depth that is more or less than one-half the width.

Exemplary intermediate plates 120, 120' and endplates 140, 140', 160, 160' will be described with reference to FIGS. 6-9. The differences between the components of the implant assembly 100 of FIG. 6 and the implant assembly 100' of FIGS. 7-9 will be identified, otherwise the components are substantially the same. With respect to the cages, the cages 102*a*' and 102*b*' are shorter than the cages 102*a* and 102*b* and have an oval configuration instead of the round configuration of the cages 102*a* and 102*b*.

Turning to the intermediate plates 120, 120', each plate 120, 120' has a ring shaped body 122, 122' with a passage 127 therethrough. The body 122 has a circular configuration to match that of the cages 102*a*, 102*b* while the body 122' has an oval configuration to match that of the cages 102*a*', 102*b*'. Each body 122, 122' extends between opposed contact surfaces 121, 123. The contact surfaces 121, 123 are at an angle θ relative to one another. This angle θ between the contact surfaces 121, 123 creates the lordotic angle α between the central axes CAa and Cab of the cages. In the event that more than two cages are utilized, intermediate plates 120 can be positioned between respective cages 102, each with the same or different angles θ.

On each body 122, 122', a plurality of tabs 124 extend from the contact surface 121 and a plurality of tabs 126 extend from the contact surface 123. The tabs 124, 126 have shapes which complement the shape of the end openings 110 such that the tabs 124, 126 are received in and engage the end openings 110 of the respective cages 102. Engagement between the tabs 124, 126 and the end openings 110 provides rotational stability between the intermediate plates 120, 120' and the cages 102. As seen in comparing the intermediate plate 120 with the intermediate plate 120', the number and location of tabs 124, 126 may be varied. Additionally, the tabs 124, 126 may be eliminated provided the spring clips 130, described below, provide sufficient rotational stability.

A plurality of spring clips 130 extend from each contact surface 121, 123. As seen in comparing the intermediate plate 120 with the intermediate plate 120', the number and location of spring clips 130 may be varied. Each spring clip 130 includes a body 132 extending from the respective surface 121, 123 and defining a retaining ledge 134 spaced from the respective surface 121, 123. The bodies 132 may have different lengths to account for the angle between the contact surfaces 121, 123 such that each of the retaining ledges 134 on respective side of the intermediate plate 120, 120' are co-planar. With the retaining ledges 134 co-planar, the retaining ledges 134 will engage a common row of openings 108 in a respective cage 102 (see FIG. 9). Each spring clip body 132 is elastic such that it bends inward as spring clips 130 pass into the cage through passage 106, but then springs outward as the retaining ledge 134 aligns with a respective opening 108. The bodies 132 may have a tapered end surface to promote the inward bending of the spring clips 130 as they are inserted. The retaining ledges 134 thereby engage the openings 108 and axially secure the intermediate plate 120, 120' to the cages 102. If it is desired to remove the intermediate plate 120, 120' from the cages 102, the retaining ledges 134 are biased inward until they clear the openings 108 and the intermediate plate 120, 120' is easily disconnected.

Turning to the endplates 140, 140', each plate 140, 140' has a ring shaped body 142, 142' with a passage 147 therethrough. The body 142 has a circular configuration to match that of the cage 102*a* while the body 142' has an oval configuration to match that of the cage 102*a*'. Each body 142, 142' extends between opposed contact surfaces 141, 143, with the contact surface 141 being a bone contact surface and the contact surface 143 being a cage contact surface. The contact surfaces 141, 143 of the endplate 140 are at an angle β relative to one another while the contact surfaces 141, 143 of the endplate 140' are parallel to one another. The endplates 140, 140' can have an angled or parallel configuration. This angle θ, or lack of angle, between the contact surfaces 141, 143 allows the surgeon to make an implant assembly 100, 100' unique to the patient's anatomy.

On each body 142, 142', a plurality of projections 144 or the like extend from the contact surface 141 and are configured to engage the vertebrae contact surface. Various surface configurations may be utilized to achieve a desired securement with the vertebrae contact surface. Additionally, the body 142 may include radial openings 145 which promote bone growth into the endplate 140.

Similar to the intermediate plates, a plurality of tabs 146 extend from the contact surface 143. The tabs 146 have shapes which complement the shape of the end openings 110 such that the tabs 146 are received in and engage the end openings 110 of the respective cages 102. Engagement between the tabs 146 and the end openings 110 provides rotational stability between the endplates 140, 140' and the cages 102. As seen in comparing the endplate 140 with the endplate 140', the number and location of tabs 146 may be varied. Additionally, the tabs 146 may be eliminated provided the spring clips 150, described below, provide sufficient rotational stability.

A plurality of spring clips 150 extend from the contact surface 143. As seen in comparing the endplate 140 with the endplate 140', the number and location of spring clips 150 may be varied. Each spring clip 150 includes a body 152 extending from the surface 143 and defining a retaining ledge 154 spaced from the surface 143. With the endplate 140, the bodies 152 may have different lengths to account for the angle between the contact surfaces 141, 143 such that each of the retaining ledges 154 of the intermediate plate 140 are co-planar. With the endplate 140', the bodies 152 will have a common length such that the retaining ledges 154 are co-planar. With the retaining ledges 154 co-planar, the retaining ledges 154 will engage a common row of openings 108 in a respective cage 102 (see FIG. 9). Each spring clip body 152 is elastic such that it bends inward as spring clips 150 pass into the cage through passage 106, but then springs outward as the retaining ledge 154 aligns with a respective opening 108. The bodies 152 may have a tapered end surface to promote the inward bending of the spring clips 150 as they are inserted. The retaining ledges 154 thereby engage the openings 108 and axially secure the endplate 140, 140' to the cage 102. If it is desired to remove the endplate 140, 140' from the cage 102, the retaining ledges 154 are biased inward until they clear the openings 108 and the endplate 140, 140' is easily disconnected.

Turning to the endplates 160, 160', each plate 160, 160' has a ring shaped body 162, 162' with a passage 167 therethrough. The body 162 has a circular configuration to match that of the cage 102*a* while the body 162' has an oval configuration to match that of the cage 102*a'*. Each body 162, 162' extends between opposed contact surfaces 161, 163, with the contact surface 161 being a bone contact surface and the contact surface 163 being a cage contact surface. In the illustrated embodiments, the contact surfaces 161, 163 of each of the endplates 160, 160' are parallel to one another, however, it is understood that the surfaces 161, 163 may be angled relative to one another to allow the surgeon to make an implant assembly 100, 100' unique to the patient's anatomy.

On each body 162, 162', a plurality of projections 164 or the like extend from the contact surface 161 and are configured to engage the vertebrae contact surface. Various surface configurations may be utilized to achieve a desired securement with the vertebrae contact surface.

Similar to the intermediate plates, a plurality of tabs 166 extend from the contact surface 163. The tabs 166 have shapes which complement the shape of the end openings 110 such that the tabs 166 are received in and engage the end openings 110 of the respective cages 102. Engagement between the tabs 166 and the end openings 110 provides rotational stability between the endplates 160, 160' and the cages 102. As seen in comparing the endplate 160 with the endplate 160', the number and location of tabs 166 may be varied. Additionally, the tabs 166 may be eliminated provided the spring clips 170, described below, provide sufficient rotational stability.

A plurality of spring clips 170 extend from the contact surface 163. As seen in comparing the endplate 160 with the endplate 160', the number and location of spring clips 170 may be varied. Each spring clip 170 includes a body 172 extending from the surface 163 and defining a retaining ledge 174 spaced from the surface 163. With each of the endplates 160, 160', the bodies 172 will have a common length such that the retaining ledges 174 are co-planar. With the retaining ledges 174 co-planar, the retaining ledges 174 will engage a common row of openings 108 in a respective cage 102 (see FIG. 9). Each spring clip body 172 is elastic such that it bends inward as spring clips 170 pass into the cage through passage 106, but then springs outward as the retaining ledge 174 aligns with a respective opening 108. The bodies 172 may have a tapered end surface to promote the inward bending of the spring clips 170 as they are inserted. The retaining ledges 174 thereby engage the openings 108 and axially secure the endplate 160, 160' to the cage 102. If it is desired to remove the endplate 160, 160' from the cage 102, the retaining ledges 174 are biased inward until they clear the openings 108 and the endplate 160, 160' is easily disconnected.

Figure 8:
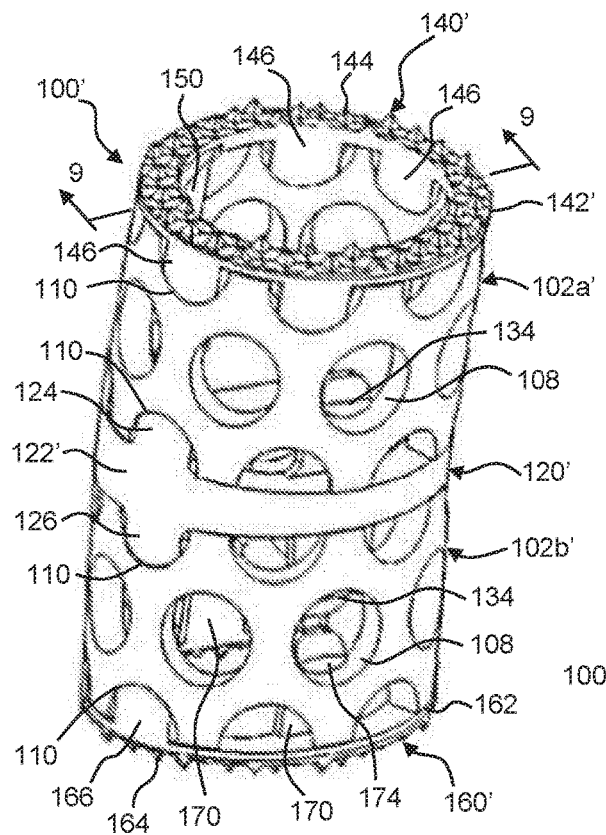
FIG. 8 is a perspective view of the implant assembly of FIG. 7 in an assembled configuration.
Figure 9:
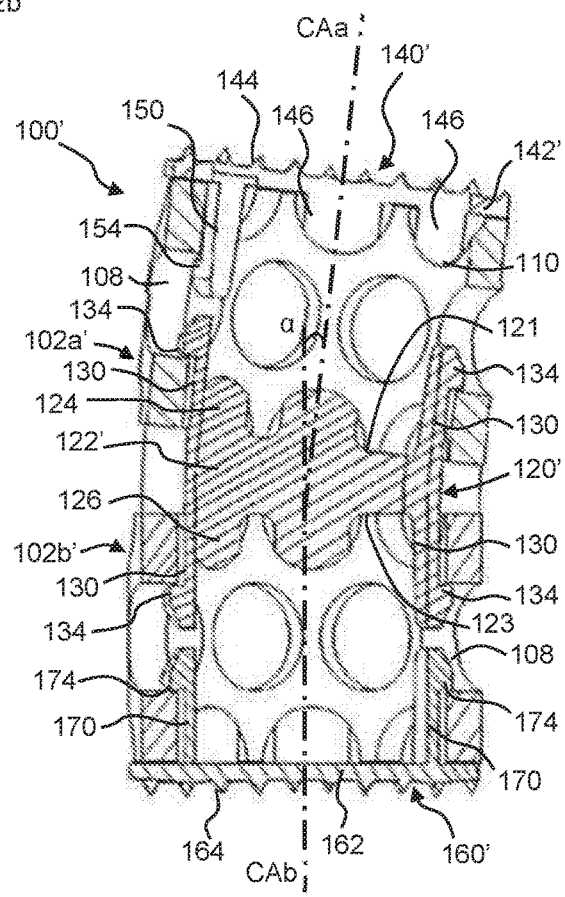
FIG. 9 is a cross-sectional view along the line 9-9 in FIG. 8.

Upon assembly of the implant assemblies 100, 100', as illustrated in FIGS. 1 and 8-9, the integrated clips 130, 150, 170 on the intermediate plate and endplates snap into the corresponding holes 108 in the mesh cages 102 for a secure fit. The quick clip system makes a secure construct while allowing for components to be removed and replaced prior to insertion into the body should the need arise. The intermediate plate 120 offers a safe and secure connection to the mesh cages 102 while providing lordosis/kyphosis at the center of the construct instead of at the end of the cage only. This allows for the body of the implant assembly to be moved away from the dura and spinal cord of the patient.

These and other advantages of the present disclosure will be apparent to those skilled in the art from the foregoing specification. Accordingly, it will be recognized by those skilled in the art that changes or modifications may be made to the above-described embodiments without departing from the broad inventive concepts. It should therefore be understood that this disclosure is not limited to the particular embodiments described herein, but is intended to include all changes and modifications that are within the scope and spirit of the disclosure as defined in the claims.

What is claimed is:

1. An implant assembly for engagement between first and second vertebrae comprising:
    a first tubular cage extending between first and second ends and having a first central axis;
    a second tubular cage extending between first and second ends and having a second central axis; and
    an intermediate plate having a body with opposed first and second contact surfaces which are at an acute angle relative to one another, the intermediate plate connected to the first tubular cage such that the first end of the first tubular cage extends along the first contact surface and connected to the second tubular cage such that the first end of the second tubular cage extends along second contact surface wherein the first and second central axes are configured to provide a lordotic angle to the implant assembly.

2. The implant assembly according to claim 1 wherein the first and second tubular cages have a given cross-sectional configuration and the intermediate plate body has the same configuration.

3. The implant assembly according to claim 2 wherein the given cross-sectional configuration is selected from circular, oval and kidney shaped.

4. The implant assembly according to claim 1 wherein the first and second tubular cages have a length selected from a plurality of pre-defined lengths or are cut to length.

5. The implant assembly according to claim 1 wherein each of the first and second tubular cages have a through passage and a plurality of radial openings which open into the respective through passages.

6. The implant assembly according to claim 5 wherein a plurality of spring clips extend from the first and second contact surfaces, each spring clip including an elastic body and a retaining ledge spaced from the respective contact surface, and wherein the spring clips are configured to extend into the passage of the respective tubular cage and each retaining ledge engages within a respective radial opening to axially secure the intermediate plate to the first and second tubular cages.

7. The implant assembly according to claim 6 wherein lengths of the elastic bodies of the spring clips extending from the first contact surface are configured such that the respective retaining ledges are co-planar and lengths of the elastic bodies of the spring clips extending from the second contact surface are configured such that the respective retaining ledges are co-planar.

8. The implant assembly according to claim 6 wherein the first end of each of the first and second tubular cages defines a plurality of end openings which open into the respective through passages and also open to the respective end surfaces of the tubular cages, and wherein a plurality of tabs extend from the first and second contact surfaces, each tab configured to engage within a respective end opening.

9. The implant assembly according to claim 1 further comprising:
   a first endplate connected to the second end of the first tubular cage and configured for securement relative to the first vertebrae; and
   a second endplate connected to the second end of the second tubular cage and configured for securement relative to the second vertebrae.

10. An implant assembly for engagement between first and second vertebrae comprising:
   a first tubular cage extending between first and second ends and having a first central axis;
   a first endplate connected to the first end of the first tubular cage and configured for securement relative to the first vertebrae;
   a second tubular cage extending between first and second ends and having a second central axis;
   a second endplate connected to the first end of the second tubular cage and configured for securement relative to the second vertebrae; and
   an intermediate plate having a body with opposed first and second contact surfaces which are at an acute angle relative to one another, the intermediate plate connected to the first tubular cage such that the second end of the first tubular cage extends along the first contact surface and connected to the second tubular cage such that the second end of the second tubular cage extends along the second contact surface, wherein the first and second central axes are at an acute angle relative to one another.

11. The implant assembly according to claim 10 wherein the first endplate has opposed first and second surfaces and the second endplate has opposed first and second surfaces and the first surface of each endplate is configured for securement relative to a respective vertebra.

12. The implant assembly according to claim 11 wherein the first surface of each endplate has a series of projections extending therefrom.

13. The implant assembly according to claim 11 wherein the first and second surfaces of at least one of the first and second end plates are at an acute angle relative to one another.

14. The implant assembly according to claim 10 wherein each of the first and second tubular cages have a through passage and a plurality of radial openings which open into the respective through passages, and
   a plurality of spring clips extend from the first and second contact surfaces of the intermediate plate and a plurality of spring clips extend from a cage contacting surface of each of the first and second endplates, each spring clip including an elastic body and a retaining ledge spaced from the respective surface, and wherein the spring clips are configured to extend into the passage of the respective tubular cage and each retaining ledge engages within a respective radial opening to axially secure the intermediate plate to the first and second tubular cages and the first and second endplates to the respective tubular cage.

15. The implant assembly according to claim 14 wherein the first and second end of each of the first and second tubular cages defines a plurality of end openings which open into the respective through passage and also open to the respective end surfaces of the tubular cage, and wherein a plurality of tabs extend from the first and second contact surfaces of the intermediate plate and a plurality of tabs extend from the cage contacting surface of each of the first and second endplates, each tab configured to engage within a respective end opening.

* * * * *